(12) United States Patent
McMaster

(10) Patent No.: US 6,727,241 B2
(45) Date of Patent: Apr. 27, 2004

(54) ANTI-INFLAMMATORY COMPOSITIONS AND METHODS OF USE

(75) Inventor: Brian McMaster, Mt. View, CA (US)

(73) Assignee: Chemocentryx, San Carlos, CA (US)

( * ) Notice: Subject to any disclaimer, the term of this patent is extended or adjusted under 35 U.S.C. 154(b) by 79 days.

(21) Appl. No.: 10/171,097

(22) Filed: Jun. 12, 2002

(65) Prior Publication Data

US 2003/0236249 A1 Dec. 25, 2003

(51) Int. Cl.[7] .................. A61K 31/55; C07D 223/10
(52) U.S. Cl. .................. 514/211.03; 514/329; 514/423; 540/485; 540/531; 544/229; 544/333; 544/334; 548/566
(58) Field of Search .................. 514/211.03, 329, 514/423; 548/566; 544/229, 333, 334; 540/531, 485

(56) References Cited

U.S. PATENT DOCUMENTS

| | | | |
|---|---|---|---|
| 4,166,452 A | 9/1979 | Generales, Jr. | 128/741 |
| 4,256,108 A | 3/1981 | Theeuwes | 128/260 |
| 4,265,874 A | 5/1981 | Bonsen et al. | 424/15 |

FOREIGN PATENT DOCUMENTS

| | | | |
|---|---|---|---|
| JP | WO 00/53600 | * | 9/2000 |
| WO | WO 9744329 | | 11/1997 |
| WO | WO 9856771 | | 12/1998 |
| WO | WO 9937619 | | 7/1999 |
| WO | WO 9937651 | | 7/1999 |
| WO | WO 99/37651 | * | 7/1999 |
| WO | WO 0053600 | | 9/2000 |

OTHER PUBLICATIONS

DeVries, M.E. et al., "On the edge: the physiological and pathophysiological role of chemokines during inflammatory and immunological responses", *Semin.Immunol.* 1999, vol. 11, pp. 95–104.

Fischer, F.R. et al., "Modulation of experimental autoimmune encephalomyelitis: effect of altered peptide ligand on chemokine and chemokine receptor expression", *J.Neuroimmunol.*, 2000, vol. 110, pp. 195–208.

Hesselgesser, J. et al., "Identification and characterization of small molecule functional antagonists of the CCR1 chemokine receptor", *J.Biol.Chem.*, 1998, vol. 273, pp. 15687–15692.

Izikson, L. et al., Resistance to experimental autoimmune encephalomyelitis in mice lacking the CC chemokine receptor (CCR)2, *J.Exp.Med.*, 2000, vol. 192, pp. 1075–1080.

Kennedy,K.J. et al., "Role of chemokines in the regulation of Th1/Th2 and autoimmune encephalomyelitis", *J.Clin.Immunol.*, 1999, vol. 19, pp. 273–279.

Liang, M. et al., "Identification and characterization of a potent, selective, and orally active antagonist of the CC chemokine receptor–1", *J.Biol.Chem.*, 2000, vol. 275, pp. 19000–19008.

Liang,M., et al., "Species selectivity of a small molecule antagonist for the CCR1 chemokine receptor", *Eur.J.Pharmacol.*, 2000, vol. 389, pp. 41–49.

Ng, H.P. et al., "Discovery of novel non–peptide CCR1 receptor antagonists", *J.Med.Chem*, 1999, vol. 42, pp. 4680–4694.

Plater–Zyberk, C. et al., "Effect of a CC chemokine receptor antagonist on collagen induced arthritis in DBA/1mice", *Immunol.Lett.*, 1997, vol. 57, pp. 117–120.

Rottman,J.B. et al., "Leukocyte recruitment during onset of experimental allergic encephalomyelitis is CCR1 dependent", *Eur.J.Immunol.*, 2000, vol. 30, pp. 2372237–7.

* cited by examiner

Primary Examiner—Dwayne C. Jones
(74) Attorney, Agent, or Firm—Brinks Hofer Gilson & Lione

(57) ABSTRACT

The present invention is directed to pharmaceutical compositions containing active compounds, which inhibit the activity of the chemokines, MIP-1α and RANTES. It also is directed to methods of treating inflammatory and immunoregulatory disorders and diseases using these pharmaceutical compositions.

9 Claims, No Drawings

ANTI-INFLAMMATORY COMPOSITIONS AND METHODS OF USE

FEDERALLY SPONSORED RESEARCH OR DEVELOPMENT

Defense Advanced Research Projects Agency (DARPA) Grant No. N65236-99-1-5420.

BACKGROUND OF THE INVENTION

The present invention is directed to pharmaceutical compositions containing active compounds and their pharmaceutically acceptable salts, which inhibit the binding of various chemokines, such as MIP-1α and RANTES, to the CCR1 receptor. It also is directed to methods of treating inflammatory and immunoregulatory disorders and diseases using these pharnmaceutical compositions.

Human health depends on the body's ability to detect and destroy foreign pathogens that might otherwise usurp valuable resources from the individual and/or induce illness. The immune system, which comprises leukocytes (white blood cells (WBCs): T and B lymphocytes, monocytes, eosinophils, basophils, and neutrophils), lymphoid tissues and lymphoid vessels, is the body's system of defense. To combat infection, B and T lymphocytes circulate throughout the body, interact with antigen-presenting cells and detect pathogens. Once an invader is detected, cytotoxic T cells are recruited to the infection site to destroy the pathogen. Chemokines act as molecular beacons for the recruitment and activation of T lymphocytes, neutrophils and macrophages, flagging pathogen battlegrounds.

While defending the individual from pathogens, the immune system can also mutiny. Inappropriate chemokine signaling has been attributed to engendering inflammatory disorders, such as rheumatoid arthritis, multiple sclerosis and others. In rheumatoid arthritis, unregulated chemokine accumulation in bone joints attracts and activates infiltrating macrophages and T-cells. The activities of these cells induce synovial cell proliferation that leads to inflammation and eventual bone and cartilage loss (DeVries, Ran et al. 1999). A hallmark of some demyelinating diseases such as multiple sclerosis is the chemokine-mediated macrophage and T cell recruitment to the central nervous system (Kennedy and Karpus 1999). Chemokine recruitment of destructive WBCs to transplants.has been implicated in their subsequent rejection (DeVries, Ran et al. 1999). Because chemokines play pivotal roles in inflammation and lymphocyte development, the ability to specifically manipulate their activity will have enormous impact on ameliorating and halting diseases that currently have no satisfactory treatment. In addition, transplant rejection may be minimized without the generalized and complicating effects of costly immunosuppressive pharmaceuticals.

Chemokines, a group of greater than 40 small peptides (7–10 kD), ligate receptors expressed on WBCs that signal through G-protein-coupled signaling cascades to mediate their chemotractant and chemostimulant functions. Receptors may bind more than one ligand; for example, the receptor CCR1 ligates RANTES (regulated on activation normal T cell expressed), MIP-1α (macrophage inflammatory protein) and MIP-1β chemokines. To date, 24 chemokine receptors are known. The sheer number of chemokines, multiple ligand binding receptors, and different receptor profiles on WBCs allow for tightly controlled and specific immune responses (Rossi and Zlotnik 2000). Chemokine activity can be controlled through the modulation of their corresponding receptors, treating related inflammatory and immunological diseases and enabling organ and tissue transplants.

The receptor CCR1 and its chemokine ligands, including, for example MIP-1α MIP-1β, and RANTES, represent promising therapeutic targets since they have been implicated in rheumatoid arthritis, transplant rejection (both reviewed in (DeVries, Ran et al. 1999)), and multiple sclerosis (Fischer, Santambrogio et al. 2000; Izikson, Klein et al. 2000; Rottman, Slavin et al. 2000). In fact, function-blocking antibodies, modified chemokine receptor ligands and small organic compounds have been discovered, some of which have been successfully demonstrated to prevent or treat some chemokine-mediated diseases (reviewed in (Rossi and Zlotnik 2000)). Notably, in an experimental model of rheumatoid arthritis, disease development is diminished when a signaling-blocking, modified-RANTES ligand is administered (Plater-Zyberk, Hoogewerf et al. 1997). While function-blocking antibody and small peptide therapies are promising, they suffer from the perils of degradation, extremely short half-lives once administered, and prohibitive expense to develop and manufacture characteristic of most proteins. Small organic compounds are preferable since they often have longer half lives in vivo, require fewer doses to be effective, can often be administered orally, and are consequently less expensive. Some organic antagonists of CCR1 have been previously described (Hesselgesser, Ng et al. 1998; Ng, May et al. 1999; Liang, Mallari et al. 2000; Liang, Rosser et al. 2000). Because such compounds have been shown to be effective in treating disease in some animal models (Liang, Mallari et al. 2000), it is desirable to have more compounds in the pharmaceutical arsenal in the art. The applicants have identified effective organic antagonists to CCR1 that promise to be important tools in this arsenal.

Piperazine derivatives of the type disclosed herein are known anti-inflammatory agents (See for example, WO98/56771, WO97/44329, WO99/37651, WO99/37619, WO00/53600). The specific piperazine derivatives disclosed herein have not previously been identified as antagonists to CCR1.

BRIEF SUMMARY OF THE INVENTION

In one embodiment, this invention provides compositions comprising a pharmaceutically acceptable carrier and an active compound that inhibits the binding of various chemokines, including for example MIP-1α and RANTES, to the CCR1 receptor.

In another embodiment, this invention provides methods for blocking the CCR1 receptor by administering an active compound that inhibits the activity of various chemokines, including for example MIP-1α and RANTES.

In another embodiment, this invention provides methods for treating inflammatory and immunoregulatory disorders and diseases by administering the compositions of the present invention.

DETAILED DESCRIPTION OF THE INVENTION

The present invention provides compositions that comprise a pharmaceutically acceptable carrier and an active compound inhibits the binding of various chemokines, including for example the major ligands MIP-1α, MIP-1β, MIP-1δ, myeloid progenitor inhibitory factor-1 (MPIF-1), hemofiltrate C-C-1 (HCC-1), leukotactin and RANTES, to the CCR1 receptor.

The compositions of the present invention are useful for treating inflammatory disorders.

Definitions

"Alkyl" refers to a saturated aliphatic group, including a straight-chain alkyl group, branched-chain alkyl group, or cycloalkyl group. In preferred embodiments, a straight chain or branched chain alkyl has 10 or fewer carbon atoms in its backbone, and more preferably 6 or fewer and most preferred 4 or fewer. Likewise, preferred cycloalkyls have from 3–10 carbon atoms in their ring structure, and more preferably have 3–6 carbons in the ring structure. Exemplary alkyl groups include, but are not limited to, methyl, ethyl, propyl, isopropyl, cyclopropyl, butyl, iso-butyl, tert-butyl, sec-butyl, cyclobutyl, pentyl, hexyl, cyclohexyl and the like. Methyl and ethyl are preferred.

"Alkoxy" refers to an alkyl group, as previously defined, attached to the parent molecular moiety through an oxygen atom. Exemplary alkoxy groups include, but are not limited to, methoxy, ethoxy, propoxy, isopropoxy, n-butoxy, tert-butoxy, neopentoxy and n-hexoxy.

"Aryl" refers to any monovalent aromatic carbocyclic group of 5 to 10 carbon atoms. The aryl group can be bicyclic (i.e. phenyl (or Ph)) or polycyclic (i.e. naphthyl) and can be unsubstituted or substituted. Preferred aryl groups include phenyl, naphthyl, furyl, thienyl, pyridyl, indolyl, quinolinyl or isoquinolinyl.

"Haloalkyl" refers to an alkyl group, as defined above, substituted by one or more halogen atoms. Exemplary haloalkyl groups include, but are not limited to, trifluoromethyl, difluoromethyl, trichloromethyl, chloroethyl, bromobutyl, 2-trifluoroethyl, 1-fluoromethyl-2-fluoroethyl, 3-bromo-2-fluoropropyl, 1-bromomethyl-2-bromoethyl, and the like. Trifluoromethyl is particularly preferred.

"Halogen" refers to a fluorine, chlorine, bromine and iodine.

"Heterocyclyl" refers to a stable, saturated, partially unsaturated, or aromatic group containing 5 to 10, preferably 5 or 6, ring atoms. The ring can be substituted 1 or more times with a substituent. The ring can be mono-, bi- or polycyclic. The heterocyclyl group consists of carbon atoms and from 1 to 3 heteroatoms independently selected from the group consisting of nitrogen, oxygen, and sulfur. Examples heterocyclyl groups include acridine, benzathiazoline, benzimidazole, benzofuran, benzopyran, benzoxazoline, benzothiapene, benzthiazole, benzothiophenyl, carbazole, cinnoline, furan, imidazole, 1H-indazole, indole, isoindole, isoquinoline, isothiazole, morpholine, oxazole (i.e. 1,2,3-oxadiazole), phenazine, phenothiazine, phenoxazine, phthalazine, piperidine, piperazine, pteridine, purine, pyrazine, pyrazole, pyridazine, pyridine, pyrimidine, pyrrole, quinazoline, quinoline, quinoxaline, tetrahydrofuran, tetrahydroquinolinyl, 1,2,3,4-tetrahydroisoquinolinyl, tetrahydrothienyl and its sulfoxide and sulfone derivatives, thiamorpholine, thiazole, 1,3,4-thiadiazole, thiene, thiophene, 1,3,5-triazines, triazole (i.e. 1,2,3-triazole), and the like.

"Substituted" means that the moiety contains at least one, preferably 1–3 substituent(s). Suitable substituents include hydrogen (H) and hydroxyl (—OH), amino (—NH$_2$), oxy (—O—), carbonyl (—CO—), thiol, alkyl, alkenyl, alkynyl, alkoxy, halo, nitrile, nitro, aryl and heterocyclyl groups. These substituents can optionally be further substituted with 1–3 substituents. Examples of substituted substituents include carboxamide, alkylmercapto, alkylsulphonyl, alkylamino, dialkylamino, carboxylate, alkoxycarbonyl, alkylaryl, aralkyl, alkylheterocyclyl, and the like.

Compounds that Inhibit the Activity of the Chemokines. MIP-1α and RANTES

In one embodiment, the active compound of the present invention is a compound of the formula (1):

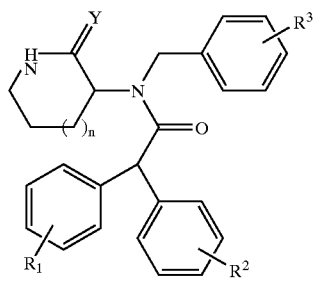

where n is 0, 1, or 2;
Y is oxygen or sulfur;
$R^1$, $R^2$, and $R^3$ are each, independently, hydrogen, alkyl, alkoxy, halogen, haloalkyl or nitro.

Preferably, the active compound of the formula (2):

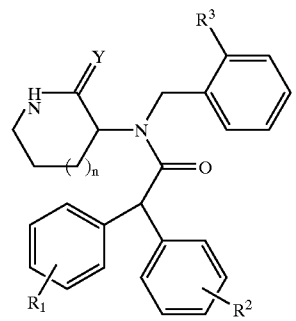

where n is 0, 1, or 2;
Y is oxygen or sulfur; and
$R^1$, $R^2$, and $R^3$ are each, independently, hydrogen, alkyl, alkoxy, halogen, haloalkyl or nitro.

Particularly preferred compounds (1) include those where $R^1$ and $R^2$ are hydrogen and $R^3$ is halogen (particularly preferably chlorine or fluorine) or hydrogen.

Compounds useful in this invention are commercially available or can be made from known procedures (See e.g., FR 1,441,071 and JP 63041907).

Testing

To demonstrate that the compounds of the present invention are antagonists of the CCR1 receptor, one can determine if they inhibit the activity of the chemokines, MIP-1α and RANTES. Preferably such compounds have the following characteristics:

(1) potently inhibit binding of the chemokines, MIP-1α or RANTES, to the CCR1 receptor;

(2) significant inhibition of the $Ca^{2+}$ response to CCR1; and (3) limited non-specific $Ca^{2+}$ response.

Standard in vitro binding assays may be employed to demonstrate the affinity of the compounds for the CCR1 receptor (thereby inhibiting the activity of MIP-1α and RANTES by competitive binding to the receptor). See examples below. Preferably, the active compounds exhibit an $IC_{50}$ value of <10 µM, more preferably <5 µM, most preferably <1 µM.

Compounds that inhibit the activity of MIP-1α and RANTES affect intracellular $Ca^{2+}$ concentrations in MIP-1α and RANTES stimulated cells. Ligand binding to the CCR1 receptor results in G-protein induced activation of phospholipase C, which leads to the conversion of phosphatidyl inositol phosphate into inositol phosphate and diacylglycerol. Inositol phosphate in turn binds to a receptor located at intracellular sites to release $Ca^{2+}$ into the cytoplasm. In addition to $Ca^{2+}$ concentrations increases due to release from intracellular stores, binding of inositol phosphate to its receptor leads to an increased flux of extracellular calcium across the membrane and into the cell. Thus, the activation of the CCR1 receptor by MIP-1α and RANTES, and, subsequently, inhibition of the activation by the compounds of the invention can be determined by assaying for an increase in free intracellular $Ca^{2+}$ levels. Typically, this can be achieved by the use of calcium-sensitive fluorescent probes such as quin-2, fura-2 and indo-1. See examples below. The affect of the active compounds to block the $Ca^{2+}$ response depends on the amount of active compound and chemokine present. Generally, when 10 nM of chemokine is present, 10 μM of active compound should produce 20 to 100% inhibition of the $Ca^{2+}$ response.

To determine whether the active compound produces a non-specific $Ca_{2+}$ response can be determined by adding active compound and measuring the described $Ca_{2+}$ response as described above and subsequently adding a known antagonist for another chemokine receptor (such as bradykinin or SDF-1, a CXCR4 ligand). A comparable response indicates that the active compound is non-specifically binding.

Pharmaceutical Compositions

The pharmaceutical compositions for the administration of the active compounds may conveniently be presented in dosage unit form and may be prepared by any of the methods well known in the art of pharmacy. All methods include the step of bringing the active compound into association with the carrier that, constitutes one or more accessory ingredients. In general, the pharmaceutical compositions are prepared by uniformly and intimately bringing the active compound into association with a liquid carrier or a finely divided solid carrier or both, and then, if necessary, shaping the product into the desired formulation. In the pharmaceutical composition the active compound is included in an amount sufficient to produce the desired effect upon the process or condition of diseases.

The pharmaceutical compositions containing the active compound may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of The present invention are employed. (For purposes of this application, topical application shall include mouth washes and gargles.)

The pharmaceutical composition and method of the present invention may further comprise other therapeutically active compounds as noted herein which are usually applied in the treatment of the above mentioned pathological conditions.

In the treatment or prevention of conditions which require chemokine receptor modulation an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150;0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Method of Blocking the CCR1 Receptor

The present invention also provides a method of inhibiting the binding of MIP-1α or RANTES to the CCR1 receptor, by contacting the compositions described above with a cell that expresses the CCR1 receptor under conditions suitable for inhibiting the binding of the chemokine to the CCR1 receptor.

Methods of Treating Inflammatory and Immunoregulatory Disorders and Diseases The present invention also provides a method of treating an inflammatory disease, by administering a therapeutically effective amount of the compositions described above to a patient in need thereof for a time sufficient to treat the inflammatory disease. "Treating" refers to the preventing, inhibiting or relieving the disorder or symptoms thereof.

CCR1 provides a target for interfering with or promoting eosinophil and/or lymphocyte function in a mammal, such as a human. Compounds that inhibit CCR1, are particularly useful for modulating eosinophil and/or lymphocyte function for therapeutic purposes. Accordingly, the present invention is directed to compounds which are useful in the prevention and/or treatment of a wide variety of inflammatory and immunoregulatory disorders and diseases.

For example, an instant compound that inhibits one or more functions of CCR1 may be administered to inhibit (ice., reduce or prevent) inflammation. As a result, one or more inflammatory processes, such as leukocyte emigration, chemotaxis, exocytosis (e.g., of enzymes, histamine) or inflammatory mediator release, can be inhibited. For example, eosinophilic infiltration to inflammatory sites (e.g., in asthma) can be inhibited according to the present method.

Similarly, an instant compound that promotes one or more functions of CCR1 is administered to stimulate (induce or enhance) an inflammatory response, such as leukocyte emigration, chemotaxis, exocytosis (e.g., of enzymes, histamine) or inflammatory mediator release, resulting in the beneficial stimulation of inflammatory processes. For example, eosinophils can be recruited to combat parasitic infections.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the method of the present invention. In a preferred embodiment, the disease or condition is one in which the actions of eosinophils and/or lymphocytes are to be inhibited or promoted, in order to modulate the inflammatory response.

Diseases or conditions of humans or other species which can be treated with inhibitors of CCR1, include, but are not limited to: inflammatory or allergic diseases and conditions, including respiratory allergic diseases such as asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersentitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies; autoimmune diseases, such as rheumatoid arthritis, psoriatic arthritis, multiple sclerosis, leukoencephalopathy, encephalomyelitis, Alzheimer's disease, systemic lupus erythematosus, myasthenia gravis, juvenile onset diabetes; glomerulonephritis, autoimmune thyroiditis, Behcet's disease; Guillian-Barre syndrome, acute cell-mediated transplant rejection (such as renal transplant rejection), graft rejection (e.g., in transplantation), including allograft rejection or graft-versus-host disease; uricaria, angioderma, inflammatory bowel diseases, such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinphilic myositis, eosinophilic fascuitis; cancers with leukocyte infiltration of the skin or organs. Other diseases or conditions in which undesirable inflammatory responses are to be inhibited can be treated, including, but not limited to, reperfusion injury, restenosis, atherosclerosis, certain hematologic malignancies, cytokine-induced toxicity (e.g., septic shock, endotoxic shock), polymyositis, dermatomyositis. The compounds of the present invention are accordingly useful in the prevention and treatment of a wide variety of inflammatory and immunoregulatory disorders and diseases.

Standard in vivo assays that may be employed to demonstrate the compositions of the present invention are useful for treating inflammatory disorders include the animal model for experimental autoimmune encephalomyelitis model for multiple sclerosis and the adjuvant-induced arthritis model for rheumatoid arthritis.

The compositions of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharnmaceutically acceptable carriers, adjuvants and vehicles appropriate for each route of administration. In addition to the treatment of warm-blooded animals such as mice, rats, horses, cattle, sheep, dogs, cats, monkeys, etc., the compositions of the invention are effective for use in humans.

Combined Therapies

Combined therapy to modulate chemokine receptor activity and thereby prevent and treat inflammatory and immunoregulatory disorders and diseases, as noted above, is illustrated by the combination of the compounds of this invention and other compounds which are known for such utilities.

For example, in the treatment or prevention of inflammation, the present compounds may be used in conjunction with an anti-inflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal anti-inflammatory agent, or a cytokine-suppressing anti-inflammatory agent, for example with a compound such as acetaminophen, aspirin, codeine, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, epinephrine, naphazoline, xylometazoline, propylhexedrine, or levo-desoxy-ephedrine; an anti-itussive such as codeine, hydrocodone, caramiphen, carbetapentane, or dextramethorphan; a diuretic; and a sedating or non-sedating antihistamine.

The following examples are intended to illustrate the present invention without limitation.

EXAMPLES

Example 1

Materials and Methods
A. Compound Collections

The compound collection used herein consists of small molecules obtained from commercial vendors. Source plates contained individual compounds at 1 or 5 mg/ml in dimethyl sulfoxide (DMSO). From these CLIP (compound library in pools) plates were made, where 10 compounds were added per well and diluted to a concentration of 5–50 μg/ml with 20% DMSO. An aliquot of 20 μl of each mixture was put into test plates, which were stored at −20° C. until use.

B. Cells

CCR1 Transfectants

CCR1-NSO Cells

A CCR1 expressing stable transfectant cell line (CCR1-NSO) was cultured in Iscove's Modified Dulbecco's Medium (IMDM) with 4.5 g/L glucose, 5% fetal bovine serum (FBS), 10 mN HCl, 250 μg/L xanthine (from xanthine 100× stock in 1N NaOH), 15 μg/L hypoxanthine (from hypoxanthine 100× stock in 0.1N NaOH), 10 mg/L thymidine (from thymidine 100× stock in $H_2O$), 50 μM β-mercaptoethanol (BME) (from BME 1000× stock in $H_2O$), and 1.5 mg/L mycophenolic acid (from 2.5 mg/ml mycophenolic acid stock in ethanol). The cells were grown in 5% $CO_2$/95% air, 100% humidity, 37° C. and harvested when the concentration was between $0.5-1.0 \times 10^6$ cells/ml. Cells were subcultured twice weekly at 1:4.

CCR1–293 Cells

Human embryonic kidney adenovirus-transformed cell line 293 (American Type Culture Collection (ATCC); Manassas, Va.) was stably transfected with human CCR1. The pIRESpuro vector (Clontech; Palo Alto, Calif.) was engineered to contain a prolactin signal sequence and FLAG-epitope cloned into the EcoRV-Not I restriction sites. A human CCR1 cDNA clone was subcloned into the Not I site, such that the insert was operably linked to the strong pCMV promoter. Cells were grown under selection with 2 μg/ml puromycin in Dubecco's Modified Eagle's Medium supplemented with 2 mM L-glutamine, 1.5 g/L sodium bicarbonate, 0.1 mM non-essential amino acids, 1.0 mM sodium pyruvate, 10% fetal bovine serum under 5% $CO_2$/95% air, 100% humidity, at 37° C. Cells were subcultured twice weekly at 1:5 and harvested at $1 \times 10^6$ cells/ml.

THP-1 Cells

THP-1 cells were obtained from ATCC and cultured as a suspension in RPMI-1640 medium supplemented with 2 mM L-glutamine, 1.5 g/L sodium bicarbonate, 4.5 g/L glucose, 10 mM HEPES, 1 mM sodium pyruvate, 0.05% 2-mercaptoethanol and 10% FBS. Cells were grown under 5% $CO_2$/95% air, 100% humidity at 37° C. and subcultured twice weekly at 1:5 and harvested at $1 \times 10^6$ cells/ml.

C. Assays

Inhibition of CCR1 Ligand Binding

CCR1 expressing cells were centrifuged and resuspended in assay buffer (20 mM HEPES pH 7.1, 140 mM NaCl, 1 mM $CaCl_2$, 5 mM $MgCl_2$, and with 0.2% bovine serum albumin) to a concentration of $5.6 \times 10^6$ cells/ml (CCR1-NSO) or $2.2 \times 10^6$ cells/ml (CCR10293.). Screening assays were set up as follows. First, 0.09 ml of cells ($5 \times 10^5$ CCR1-NSO cells/well or $2 \times 10^5$ CCR1–293 cells/well) was added to the assay plates containing the compounds, giving a final concentration of ~2–10 µM each compound. Then 0.09 ml of $^{125}I$ labeled MIP-1α (obtained from Amersham; Piscataway, N.J.) diluted in assay buffer to a final concentration of ~50 pM, yielding ~30,000 cpm per well, was added, the plates sealed and incubated for approximately 3 hours at 4° C. on a shaker platform. Reactions were aspirated onto GF/B glass filters pre-soaked in 0.3% polyethyleneimine (PEI) solution, on a vacuum cell harvester (Packard Instruments; Meriden, Conn.). Scintillation fluid (50 µl; Microscint 20, Packard Instruments) was added to each well, the plates were sealed and radioactivity measured in a Top Count scintillation counter (Packard Instruments). Control wells containing either diluent only (for total counts) or excess MIP-1α or MIP-1β (1g/ml, for non-specific binding) were used to calculate the percent of total inhibition for each set of compounds. After testing the CLIP plates, wells with 40% or greater inhibition were confirmed. If confirmed, the individual compounds of the CLIP's were tested for reactivity (deconvolution step). $IC_{50}$ values are those concentrations required to reduce the binding of labeled MIP-1α to the receptor by 50%.

Calcium Mobilization

To detect the release of intracellular stores of calcium, cultured cells were incubated with 3 µM of INDO-1AM dye (Molecular Probes; Eugene, Oreg.) in cell media for 45 minutes at room temperature and washed with phosphate buffered saline (PBS). After INDO-1AM loading, the cells were resuspended in flux buffer (Hank's balanced salt solution (HBSS) and 1% FBS). Calcium mobilization was measured using a Photon Technology International spectrophotometer (Photon Technology International; New Jersey) with excitation at 350 nm and dual simultaneous recording of fluorescence emission at 400 nm and 490 nm. Relative intracellular calcium levels were expressed as the 400 nm/490 nm emission ratio. Experiments were performed at 37° C. with constant mixing in cuvettes each containing $10^6$ cells in 2 ml of flux buffer. The chemokine ligands may be used over a range from 1 to 100 nM. The emission ratio was plotted over time (typically 2–3 minutes). Candidate ligand blocking compounds (10 to 20 µM) were added at 10 seconds, followed by chemokines at 60 seconds (MIP-1α; R&D Systems; Minneapolis, Minn.) and control chemokine (bradykinin; ICN Pharmaceutical, Costa Mesa, Calif.) at 150 seconds. In some experiments, candidate blocking compounds and cells were added simultaneously, and MIP-1α was added 40 seconds later.

Chemotaxis Assays

Chemotaxis assays were performed using 5 µm pore polycarbonate, polyvinylpyrrolidone-coated filters in 96-well chemotaxis chambers (Neuroprobe; Gaithersburg, Md.). Stromal-derived factor (SDF-1) was used as a specificity control. The lower chamber was loaded with 29 µl, of 0.1 nM MIP-1α and varying amounts of an inhibitor; the top chamber contained 100,000 THP-1 cells in 20 µl. The chambers were incubated 1–2 hours at 37° C., and the number of cells in the lower chamber quantified by the CyQuant assay (Molecular Probes), a fluorescent dye method that measures nucleic acid content and microscopic observation.

Example 2

Identification of Inhibitors of CCR1 Ligation of MIP-1α

A. Assay

To identify small organic molecules that prevent the receptor CCR1 from binding ligand, an assay was employed that detected radioactive ligand (MIP-1α) binding to cells expressing exogenous CCR1 on the cell surface. If a compound inhibited binding, whether competitive or not, then fewer radioactive counts would be observed when compared to uninhibited controls.

A NSO murine myeloma cell line (CCR1-NSO) and a human embryonic kidney (HEK) carcinoma cell line (CCR1–293) were constructed that constitutively expressed human CCR1 on the cell surface; these cells lack other chemokine receptors that bind MIP-1α. Equal numbers of cells were added to each well in the CLIP plate, where each pool contained 10 candidate organic compounds. The cells were then incubated with radio labeled MIP-1α. Unbound ligand was removed by washing the cells, and bound ligand was determined by quantifying radioactive counts. Cells that were incubated without any organic compound gave total counts; non-specific binding was determined by incubating the cells with unlabeled ligand and labeled ligand. Percent inhibition was determined by the equation:

$$\% \text{ inhibition} = 1 - [(\text{sample cpm}) - (\text{nonspecific cpm})]/[(\text{total cpm}) - (\text{nonspecific cpm})] \times 100$$

B. Inhibitors from Compound Library Identified Using CCR1-NSO Cells

In the first set of tested compounds, the normalized standard deviation was 19%; therefore, significant inhibition was determined to be greater than 38%; 40% inhibition was the selected threshold. Of the number of wells tested, the contents of 58 wells inhibited MIP-1α binding of 40% or greater. The contents of these 58 wells were retested in the CLIP format where 6 inhibited binding by 40% or more. This result indicated that at least one of the 10 compounds in each of the 6 wells inhibited MIP-1α binding to CCR1. To determine which of the 10 compounds in each well inhibited CCR1 ligation of MIP-1α, the pools were deconvoluted by testing each of the compounds individually for inhibitory activity in the assay. Because some compounds may act together to inhibit binding and deconvolution assays only tested compounds individually, compounds that were effective in combination but not singly were not found in this experiment. Three candidate compounds were identified:

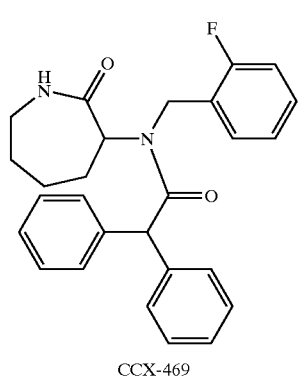

(1)

CCX-469

(2)

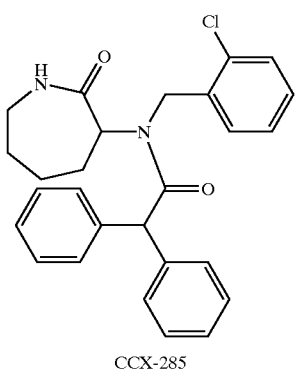

CCX-285 and (3)

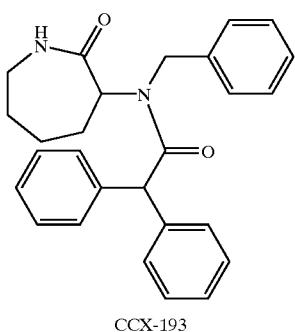

CCX-193

In a screen of a second set of compounds, the normalized standard deviation was 17%, indicating that inhibition activity of 34% or more was significant; again, a 40% threshold was used. These CLIPs yielded 39 wells that exhibited greater than 40% inhibition. When screened a second time as CLIPs, 14 of these wells decreased ligand by greater than 40%. Testing the compounds singly identified 13 inhibitory candidates:

(4)

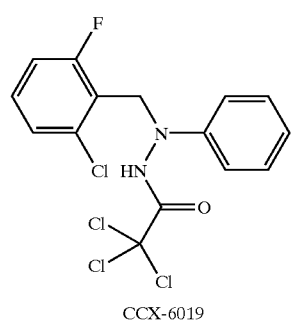

CCX-6019

(5)

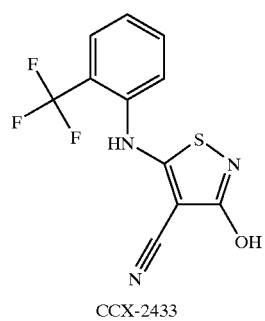

CCX-2433

(6)

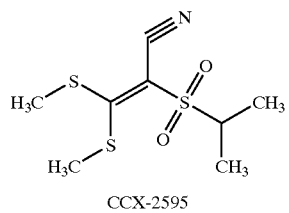

CCX-2595

(7)

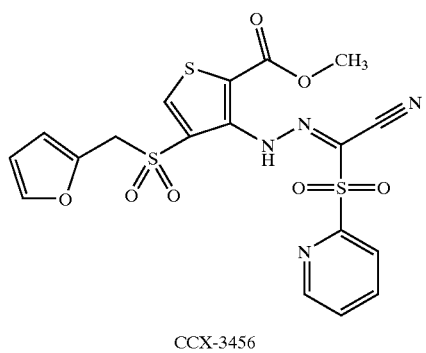

CCX-3456

(8)

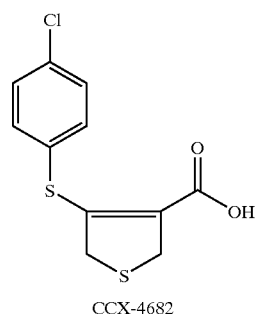

CCX-4682

(9)

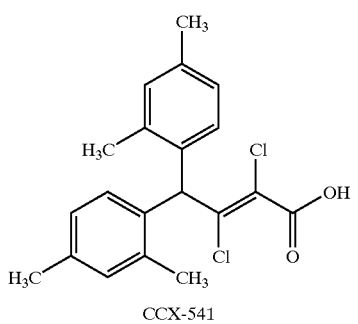

CCX-541

(10)

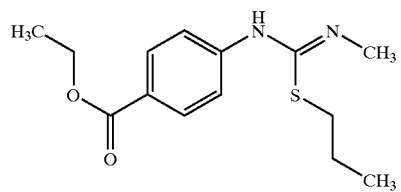

CCX-238

(11)
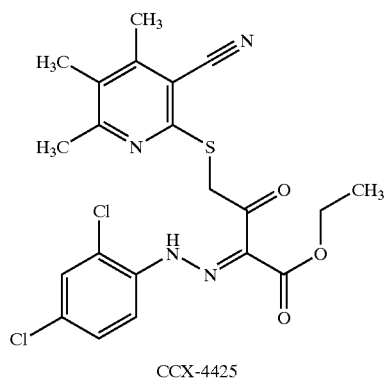
CCX-4425

(12)
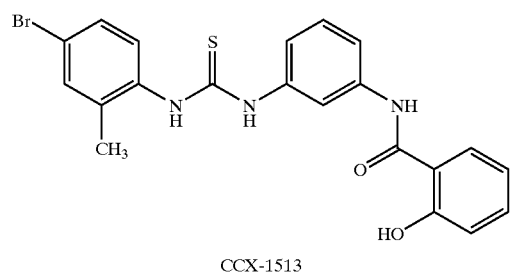
CCX-1513

(13)
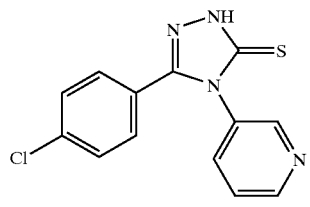
CCX-3493

(14)
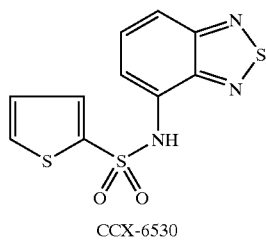
CCX-6530

(15)
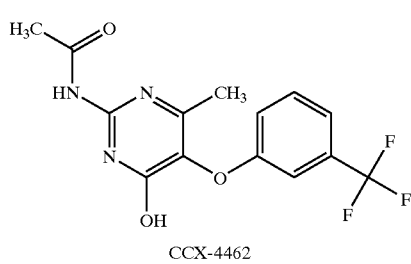
CCX-4462

(16)
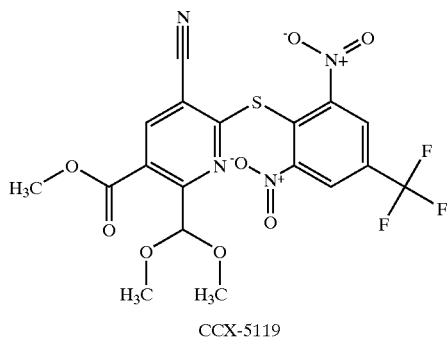
CCX-5119

C. Inhibitors From Compound Library Identified Using CCR1–293 Cells

Using the CCR1–293 cells, which express CCR1 at higher levels, resulted in improved noise to signal ratios and a normalized standard deviation that was around 10%. Screening a first set of compounds, 46 wells exhibited greater than 20% inhibition of ligand binding in the initial screen, 10 wells in the CLIP format inhibited ligand binding in a second screening. Testing the compounds individually identified 6 candidates:

(17)
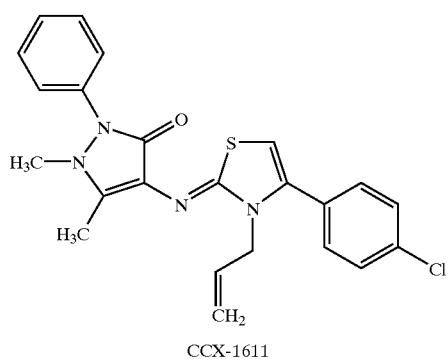
CCX-1611

(18)
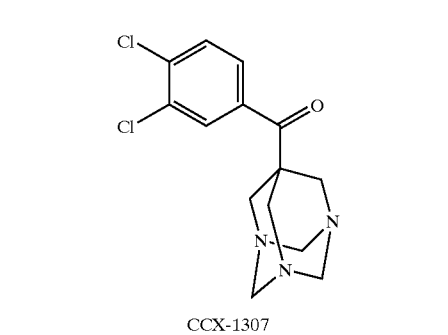
CCX-1307

(19)
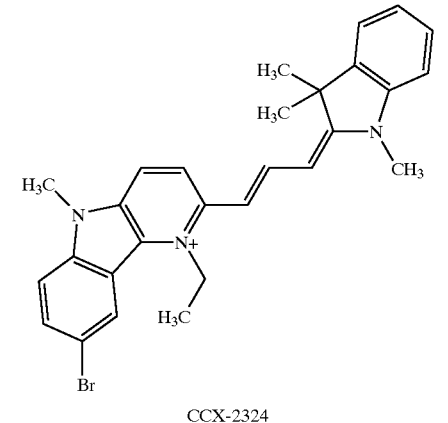
CCX-2324

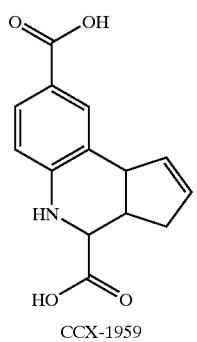

CCX-1959 (20)

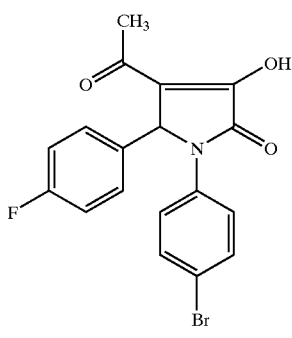

CCX-5062 (23)

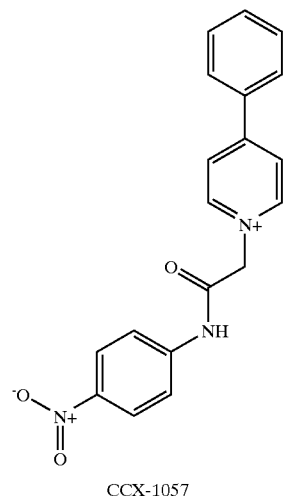

CCX-1057 (21)

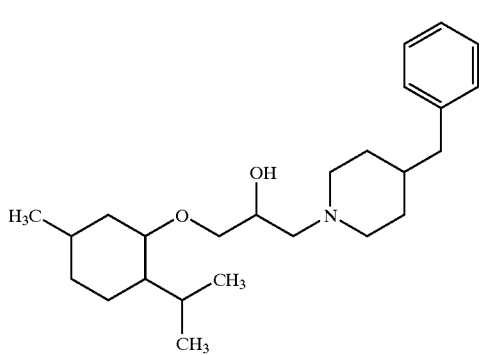

CCX-3345 (24)

and

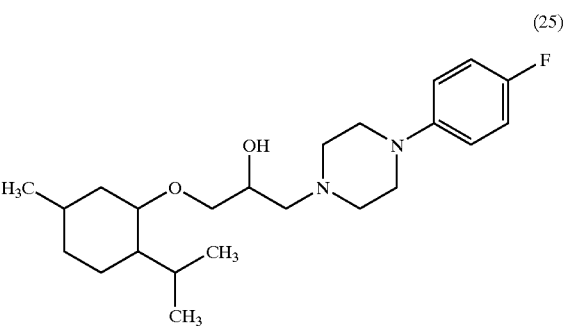

CCX-3343 (25)

and

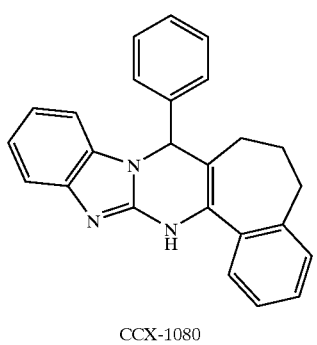

CCX-1080 (22)

As for the assays with the first set of compounds using CCR1–293 cells, screens of a second set of compounds also had smaller normalized standard deviations, most likely due to the use of these cells. Of 35 CLIP wells that inhibited binding in a first trial, 8 wells were confirmed. Individual testing of the compounds identified 3 candidates:

Example 3

Dose Response Curves

To ascertain a candidate compound's affinity for CCR1 as well as confirm its ability to inhibit ligand binding, inhibitory activity was titered over $1 \times 10^{-8}$ to $1 \times 10^{-4}$ M range of compound concentration. The assay was essentially the same as for the CLIP screens, except the amount of compound was varied; cell number and ligand concentration were held constant. Only those compounds that were commercially available at the time of the experiments were titered. Of the 22 candidates identified, the following 16 were subjected to dose response experiments: CCX-3343, CCX-1057, CCX-1307, CCX-1513, CCX-238, CCX-3345, CCX-3493, CCX-4425, CCX-4462, CCX-4682, CCX-469, CCX-5062, CCX-5119, CCX-541, CCX-6019 and CCX-6530.

Tested compounds that failed to inhibit MIP-1α binding in a dose-dependent manner were CCX-238, CCX-4425, and CCX-4462. Compounds with inhibitory activity varied in their affinity for CCR1 as presented in Table 1.

TABLE 1

Affinity values for CCR1-MIP-1α binding, arranged from highest affinity to lowest.

| Compound No. | Cells | $IC_{50}$ (Inhibition Constant; μM) |
|---|---|---|
| CCX-1959 | NSO | 0.36 |
| CCX-541 | NSO | 0.4 |
| CCX-469 | NSO/293 | 0.6/2 |
| CCX-3493 | NSO | 1.7 |
| CCX-2324 | 293 | 2* |
| CCX-1307 | 293 | 2* |
| CCX-1080 | 293 | 2* |
| CCX-1057 | 293 | 2* |
| CCX-3493 | 293 | 18 |
| CCX-6019 | NSO | 25 |
| CCX-4682 | NSO | 44 |
| CCX-5119 | 293 | 45 |
| CCX-6530 | NSO | n.d. |
| CCX-1513 | NSO | n.d. |
| CCX-4462 | NSO | n.d. |
| CCX-5119 | NSO | n.d. | n.d., not determined (calculated).
*Partially blocked MIP-1α binding at the highest tested concentration.

The compounds CCX-541 and CCX-469 exhibited CCR1 affinities below 1 μM. Compounds CCX-5062, CCX-3345, and CCX-3343 had blocking activity, but failed to completely inhibit MIP-1α binding at the highest tested concentration; their affinities were estimated to be approximately 2 μM. Even though compounds CCX-6019, CCX-4682, CCX-1307 and CCX-1057 exhibited blocking activity, they had lower affinities for CCR1, from 18 μM to 45 μM. While many compounds were identified that were capable of inhibiting CCR1 from binding the MIP-1α ligand, only two had high CCR1 affinities: CCX-541 and CCX-469. Other lower affinity, MIP-1α binding inhibitory compounds were identified, but because the nature of the inhibition was unknown—competitive or non-competitive—it was unclear whether these compounds would be more effective in inhibiting other CCR1 ligands from binding, such as RANTES.

Example 4

CCR1 Functional Assays

CCR1 is a seven transmembrane, G-protein linked receptor. A hallmark of signaling cascades induced by the ligation of such receptors is the pulse-like release of calcium ions from intracellular stores. Calcium mobilization assays were performed to determine if the candidate MIP-1α inhibitory compounds were able to also block CCR1 signaling. To be useful, candidate compounds able to inhibit specifically ligand binding and signaling were desired.

Calcium ion release in response to MIP-1α binding was measured using the cell permeable INDO-1/AM indicator, which fluoresces in the presence of free, but not chelated, calcium ions. CCR1–293 or THP-1 cells were loaded with INDO-1 and assayed for calcium release in response to MIP-1α addition. To control for specificity, a second, non-CCR1 binding chemokine, bradykinin, was added, which also signals via a seven transmembrane receptor. Without compound, a pulse of fluorescent signal will be seen upon MIP-1α addition. If a compound specifically inhibits CCR1-MIP-1α signaling, then no signal pulse will be seen upon MIP-1α addition, but a pulse will be observed upon bradykinin addition. However, if a compound non-specifically inhibits signaling, then no pulse will be seen upon both MIP-1α and bradykinin addition.

As shown in Table 2, of the selected compounds that were tested, CCX-469, CCX-541, CCX-1513 and CCX-3493, only CCX-469 was able to significantly and specifically inhibit signaling from CCR1. CCX-541 and CCX-1513 had non-specific effects on calcium levels, and CCX-3493 did not affect signaling, whether MIP-1α or bradykinin induced.

TABLE 2

Inhibition of calcium signaling

| Compound | MIP-1α[1] | Bradykinin[1] | Comments |
|---|---|---|---|
| CCX-541 | n.s. | n.s. | Calcium levels increased non-specifically over time in presence of compound. |
| CCX-469 | – | + | Clear and specific inhibition of THP-1 cells. |
| CCX-1513 | n.s. | n.s. | Calcium levels increased non-specifically over time in presence of compound. |
| CCX-3493 | + | + | No inhibition. |

[1]+, pulse observed, –, no pulse observed, n.s., non-specific signal (see main text)

Example 5 (Prophetic)

One of the primary functions of chemokines is their ability to attract WBCs to 10 sites of pathogen invasion. To confirm that a compound inhibits not only MIP-1α binding and CCR1 signaling as determined by calcium mobilization, but also CCR1 function, a chemotaxis assay is employed. THP-1 myelomonocytic leukemia cells, which resemble monocytes, are used as targets for chemoattraction by MIP1α. THP-1 cells are placed in the top compartment of a microwell migration chamber, while MIP-1α and increasing concentrations of a compound are loaded in the lower chamber. In the absence of inhibitor, THP-1 cells migrate to the lower chamber in response to the MIP-1α chemokine; if a compound inhibits CCR1 function, then the majority of THP-1 cells remain in the upper chamber.

Many variations of the present invention will suggest themselves to those skilled in the art in light of the above detailed.description. Such obvious variations are within the full intended scope of the appended claims.

References

DeVries, M. E., L. Ran, et al. (1999). "On the edge: the physiological and pathophysiological role of chemokines during inflammatory and immunological responses." *Semin Immunol* 11(2): 95–104.

Fischer, F. R., L. Santambrogio, et al. (2000). "Modulation of experimental autoimmune encephalomyelitis: effect of altered peptide ligand on chemokine and chemokine receptor expression." *J Neuroimmunol* 110(1–2): 195–208.

Hesselgesser, J., H. P. Ng, et al. (1998). "Identification and characterization of small molecule functional antagonists of the CCR1 chemokine receptor." *J Biol Chem* 273(25): 15687–92.

Izikson, L., R. S. Klein, et al. (2000). "Resistance to experimental autoimmune encephalomyelitis in mice lacking the CC chemokine receptor (CCR)2 [In Process Citation]." *J Exp Med* 192(7): 1075–80.

Kennedy, K. J. and W. J. Karpus (1999). "Role of chemokines in the regulation of Th1/Th2 and autoimmune encephalomyelitis." *J Clin Immunol* 19(5): 273–9.

Liang, M., C. Mallari, et al. (2000). "Identification and characterization of a potent, selective, and orally active antagonist of the CC chemokine receptor-1." *J Biol Chem* 275(25): 19000–8.

Liang, M., M. Rosser, et al. (2000). "Species selectivity of a small molecule antagonist for the CCR1 chemokine receptor." *Eur J Pharmacol* 389(1): 41–9.

Ng, H. P., K. May, et al. (1999). "Discovery of novel non-peptide CCR1 receptor antagonists." *J Med Chem* 42(22): 4680–94.

Plater-Zyberk, C., A. J. Hoogewerf, et al. (1997). "Effect of a CC chemokine receptor antagonist on collagen induced arthritis in DBA/1 mice." *Immunol Lett* 57(1–3): 117–20.

Rossi, D. and A. Zlotnik (2000). "The Biology of Chemokines and their Receptors." *Annu. Rev. Immunol.* 18(1): 217–242.

Rottman, J. B., A. J. Slavin, et al. (2000). "Leukocyte recruitment during onset of experimental allergic encephalomyelitis is CCR1 dependent." *Eur J Immunol* 30(8): 2372–7.

What is claimed is:

1. A composition comprising a pharmaceutically acceptable carrier and a compound of the formula (1):

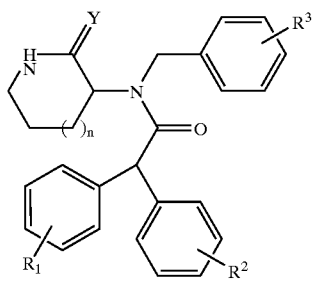

where:

n is 0, 1, or 2;

Y is oxygen or sulfur;

$R^1$, $R^2$, and $R^3$ are each, independently, hydrogen, alkyl, alkoxy, halogen, haloalkyl or nitro.

2. The composition of claim 1, wherein compound (3) is a compound of the formula (2):

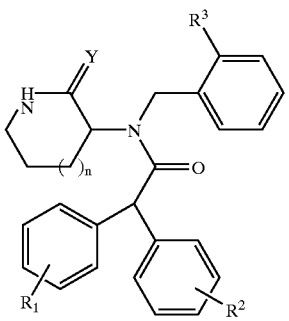

where:
n is 0, 1, or 2;
Y is oxygen or sulfur; and
$R^1$, $R^2$, and $R^3$ are each, independently, hydrogen, alkyl, alkoxy, halogen, haloalkyl or nitro.

3. The composition of claim 1, wherein $R^1$ and $R^2$ are hydrogen.

4. The composition of claim 1, wherein $R^3$ is halogen.

5. The composition of claim 4, wherein $R^3$ is chlorine or fluorine.

6. The composition of claim 1, wherein $R^3$ is hydrogen.

7. A composition comprising a pharmaceutically acceptable carrier and a compound (1):

(1)

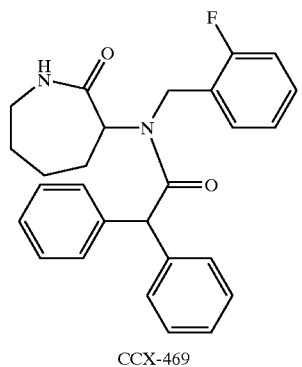

CCX-469

8. A method of inhibiting the binding of a chemokine, which is MIP-1α or RANTES, to a CCR1 receptor, comprising contacting the composition of claim 1 or 2 with a cell that expresses the CCR1 receptor for a time sufficient to inhibit the binding of the chemokine to the CCR1 receptor.

9. A method of treating an inflammatory disease, comprising administering a therapeutically effective amount of the composition of claim 1 or 2 to a patient in need thereof for a time sufficient to treat the inflammatory disease.

* * * * *

UNITED STATES PATENT AND TRADEMARK OFFICE
CERTIFICATE OF CORRECTION

PATENT NO. : 6,727,241 B2
DATED : April 27, 2004
INVENTOR(S) : Brian McMaster

It is certified that error appears in the above-identified patent and that said Letters Patent is hereby corrected as shown below:

Title page,
Item [*] Notice, delete the phrase "by 79 days" and insert -- by 199 days --

Signed and Sealed this

Twenty-fourth Day of May, 2005

JON W. DUDAS
*Director of the United States Patent and Trademark Office*